(12) United States Patent
Dixon et al.

(10) Patent No.: US 8,722,706 B2
(45) Date of Patent: *May 13, 2014

(54) TWO PHASE BIOACTIVE FORMULATIONS OF BIS-QUATERNARY PYRIDINIUM OXIME SULFONATE SALTS

(75) Inventors: Hong Dixon, Helotes, TX (US); Joseph A McDonough, Helotes, TX (US); Larry Allen Cabell, San Antonio, TX (US); Patricia Underwood, New Market, MD (US)

(73) Assignee: Southwest Research Institute, San Antonio, TX (US)

(*) Notice: Subject to any disclaimer, the term of this patent is extended or adjusted under 35 U.S.C. 154(b) by 1015 days.

This patent is subject to a terminal disclaimer.

(21) Appl. No.: 12/192,400

(22) Filed: Aug. 15, 2008

(65) Prior Publication Data

US 2010/0040692 A1 Feb. 18, 2010

(51) Int. Cl.
*A61K 31/4425* (2006.01)
*A61K 47/06* (2006.01)

(52) U.S. Cl.
CPC ............ *A61K 31/4425* (2013.01); *A61K 47/06* (2013.01)
USPC ....................................................... 514/332

(58) Field of Classification Search
CPC ........................... A61K 31/4425; A61K 47/06
See application file for complete search history.

(56) References Cited

U.S. PATENT DOCUMENTS

| | | | |
|---|---|---|---|
| 2,305,947 A | 12/1942 | Armstrong | |
| 2,816,113 A | 12/1957 | Wilson | |
| 3,135,761 A * | 6/1964 | Hackley, Jr. et al. | ......... 546/264 |
| 3,137,702 A | 6/1964 | Luttringhaus | |
| 3,629,425 A | 12/1971 | Hussain | |
| 3,929,813 A | 12/1975 | Higuchi et al. | |
| 4,128,651 A | 12/1978 | Hagedorn | |
| 4,305,947 A | 12/1981 | Bartner | |
| 4,540,602 A | 9/1985 | Motoyama et al. | |
| 4,705,777 A | 11/1987 | Lehrer et al. | |
| 4,880,610 A | 11/1989 | Constantz | |
| 5,130,438 A | 7/1992 | Hsiao et al. | |
| 5,145,684 A | 9/1992 | Liversidge et al. | |
| 5,298,504 A | 3/1994 | Sommer et al. | |
| 5,589,167 A | 12/1996 | Cleland | |

(Continued)

FOREIGN PATENT DOCUMENTS

| | | |
|---|---|---|
| EP | 1319400 | 6/2003 |
| WO | 9814587 | 4/1998 |

(Continued)

OTHER PUBLICATIONS

Garcia et al. (Walter Reed Army Institute of Research, Nov. 1, 2006, (8pgs.).*

(Continued)

*Primary Examiner* — Noble Jarrell
*Assistant Examiner* — Valerie Rodriguez-Garcia
(74) *Attorney, Agent, or Firm* — Grossman, Tucker et al

(57) ABSTRACT

The present invention relates to two phase systems of a bioactive ingredient in particle form that has limited or no solubility in a liquid medium, which provides stability to the bioactive ingredient that is similar to the bioactive ingredient when in the solid state. The bioactive ingredient may be capable of therapeutically treating for the presence of a cholinesterase inhibitor. The bio active ingredient comprises 1,1'-methylyenebis[4-[(hydroxyimino)methyl]-pyridinium] dimethanesulfonate.

5 Claims, 10 Drawing Sheets

(56) References Cited

U.S. PATENT DOCUMENTS

| | | | |
|---|---|---|---|
| 5,662,883 | A | 9/1997 | Bagchi et al. |
| 5,716,642 | A | 2/1998 | Bagchi et al. |
| 5,770,181 | A | 6/1998 | Kirkland |
| 5,902,816 | A | 5/1999 | Viner |
| 5,929,093 | A * | 7/1999 | Pang et al. ............ 514/332 |
| 6,007,845 | A | 12/1999 | Domb et al. |
| 6,117,454 | A | 9/2000 | Kreuter et al. |
| 6,355,271 | B1 | 3/2002 | Bell et al. |
| 6,395,029 | B1 | 5/2002 | Levy et al. |
| 6,656,505 | B2 | 12/2003 | Kundu et al. |
| 6,815,543 | B1 | 11/2004 | Bernardelli |
| 6,861,068 | B2 | 3/2005 | Ng et al. |
| 6,881,745 | B2 | 4/2005 | Hayes et al. |
| 7,037,528 | B2 | 5/2006 | Kipp et al. |
| 7,081,161 | B2 | 7/2006 | Genge et al. |
| 7,282,194 | B2 | 10/2007 | Sung et al. |
| 7,300,670 | B2 | 11/2007 | Venus et al. |
| 7,387,792 | B2 | 6/2008 | Hirsh et al. |
| 7,390,384 | B2 | 6/2008 | Fang et al. |
| 2003/0073619 | A1 | 4/2003 | Mahato et al. |
| 2004/0022820 | A1 | 2/2004 | Anderson |
| 2004/0256749 | A1 | 12/2004 | Chaubal et al. |
| 2004/0266890 | A1 | 12/2004 | Kipp et al. |
| 2005/0106257 | A1 | 5/2005 | Albayrak |
| 2005/0113489 | A1 | 5/2005 | Baran, Jr. et al. |
| 2005/0118108 | A1 | 6/2005 | Cowan et al. |
| 2005/0220888 | A1 | 10/2005 | Putcha et al. |
| 2006/0063662 | A1 | 3/2006 | Hata et al. |
| 2006/0183777 | A1 | 8/2006 | Huang et al. |
| 2006/0216353 | A1 | 9/2006 | Liversidge et al. |
| 2007/0093518 | A1 * | 4/2007 | Wetherell et al. ............ 514/290 |
| 2007/0134339 | A1 | 6/2007 | Jenkins et al. |
| 2007/0190160 | A1 | 8/2007 | Turos et al. |
| 2008/0145439 | A1 | 6/2008 | Lobl et al. |
| 2008/0241256 | A1 | 10/2008 | Kuhn |
| 2009/0263491 | A1 | 10/2009 | Kreuter et al. |
| 2009/0281144 | A1 * | 11/2009 | Cabell et al. ............ 514/332 |
| 2009/0304720 | A1 | 12/2009 | Kreuter et al. |

FOREIGN PATENT DOCUMENTS

| | | |
|---|---|---|
| WO | 9841188 | 9/1998 |
| WO | 0163362 | 8/2001 |
| WO | 0232402 | 4/2002 |
| WO | 2004073033 | 8/2004 |
| WO | 2005123581 | 12/2005 |
| WO | 2007/001355 A2 | 1/2007 |
| WO | 2007/084460 A2 | 7/2007 |
| WO | 2009114298 | 9/2009 |

OTHER PUBLICATIONS

Munavalli et al. (Heterocycles 1986, 24(7); 1883-1892).*
Thiermann et al. (International Journal of Pharmaceutics (1996), 137; p. 167-176).*
Chaumeil, J.C., Methods and Findings in Experimental and Clinical Pharmacology, Apr. 1998, vol. 20, No. 3, pp. 211-215.*
Garner et al. Journal of Pharmaceutical Sciences, vol. 91, Issue 1, pp. 32-40.*
Choi, International Journal of Mineral Processing vol. 74, Supplement 1, Dec. 10, 2004, pp. S165-S172.*
Chemistry and Industry; Applied Chemistry; Nigel Freestone; Nov. 7, 2005 (4 pgs).
Chemistry and Industry; New Drug Delivery Systems; Alexander T. Florence; Dec. 20, 1993 (7 pgs).
Advanstar Communications, Inc.; Pharmaceutical Technology; Vivek Kharb; Meenakshi Bhatia; Harish Dureja; Deepak Kaushik; Feb. 1, 2006 (11 pgs).
Advanstar Communications, Inc.; Pharmaceutical Technology Europe; Magdalene Radtke; Eliana B. Souto; Rainer H. Muller; Apr. 1, 2005 (4 pgs).
Dennison, et al. "Corticosteroids in rheumatoid arthritis," British Medical Journal vol. 316, pp. 789-790 (1998).
Kenalog® Creams Triamcinolone Acetonide Cream USPO.025%, 0.1 %,0.5% (Online) http://dar1ymed.n1m.nih.gOY1dai1ymed/fda/fdaDrugXsl.cfm?id=1872&type=display; retrieved Jun. 21, 2008 (8 pages).
D. Farcasiu, et al. "Evaluation of hydrogen bonding by C-13NMR" Catalysis Letters 31 (1995) 351-358.
Praetorius, et al., "Engineered Nanoparticles in Cancer Therapy," Recent Patents on Drug Delivery & Formation 2007,vol. 1 No. 1, pp. 37-51.
Biosante Pharmaceuticals, "Hormone Therapy-A Multi-Billion Dollar Market," Investor Fact Sheet Sep. 2007; www.biosantepharma.com; (2 pages).
T.Welzel, et al., "Transfection of Cells With Custom-made Calcium Phosphate Nanoparticles Coated With DNA"; The Royal Society of Chemistry 2004; J. Mater. Chem. 2004, 14, pp. 2213-2217.
S. Bisht, et al., "pDNA Loaded Calcium Phosphate Nanoparticles: Highly Efficient Non-Viral Vector for Gene Delivery"; International Journal of Pharmaceutics 288 (2005), pp. 157-168.
T.Liu, et al., "Calcium Phosphate Nanoparticles As a Novel Nonviral Vector for Efficient Transfection of DNA in Cancer Gene Therapy"; Cancer Biotherapy & Radiopharmaceuticls, vol. 20, No. 2, 2005, pp. 141-150.
A. Brioschi, et al, "Solid Lipid Nanoparticles: Could They Help . . . "; Neurological Research 2007, vol. 29, Apr. 2007; pp. 324-330.
M. Nahar, et al, "Functional Polymeric Nanoparticles: An Efficient . . . "; Critical Reviews™ In Therapeutic Drug Carrier Systems, 23(4):259-318 (2006); Begell House Inc., http://begellhouse.com; downloaded Sep. 18, 2009 from IP 129.162.1.41 by Celia Frausto.
International Search Report and Written Opinion dated Nov. 23, 2009 issued in related International Patent Application No. PCT/US0959386.
U.S. Office Action dated Dec. 9, 2010 issued in related U.S. Appl. No. 11/555,995.
Digiovanni, Jr., M.D., Cleto, Domestic Terrorism With Chemical or Biological Agents: Psychiatric Aspects, Am J Psychiatry, Oct. 1999, pp. 1500-1505, vol. 156:10.
D'Mello, G.D., Behavioural Toxicity of Anticholinesterases in Humans and Animals—A Review, Human & Experimental Toxicology, 1993, pp. 3-7, vol. 12.
Eyer, et al., Oximes—Chapter 15, Chemical Warfare Agents: Toxicology and Treatment, 2007, pp. 305-329, 2nd Edition.
Jager, et al., Toxicity of Diacetyl Monoxime and of Pyridine-2-Aldoxime Methiodide in Man, Bull John Hopkins Hosp., 1958, pp. 203-211, vol. 102.
Jamal, Goran A., Long term neurotoxic effects of organophosphate compounds, Adverse Drug React. Toxicol. Rev, 1995, pp. 85-99, vol. 14(2).
Marrs et al., Chemical Warfare Agents: Toxicology and Treatment Second Edition, 2007, pp. all. Table of contents attached electronically, physical book is cited and supplied in U.S. Appl. No. 12/702,095 which was mailed to USPTO Oct. 8, 2010.
McDonough, et al., Behavioral Correlates of Soman-Induced Neuropathology: Deficits in DRL Acquisition, Neurobehavioral Toxicology and Teratology, 1986, pp. 179-187, vol. 8.
U.S. Office Action dated Jun. 25, 2008 issued in U.S. Appl. No. 11/555,995, 23 pages.
U.S. Office Action dated Nov. 28, 2008 issued in U.S. Appl. No. 11/555,995, 8 pages.
Radic, et al., "Evaluation of HI-6 oxime: potential use in protection of human acetylcholinesterase inhibited by antineoplastic drug irinotecan and its cyto/genotoxicity in vitro," Acta Biochimica Polonica vol. 54 No. 3/2007, 583-593, Aug. 23, 2007.
Stojiljkovic, et al., "Pryidinum Oximes: Rationale for their Selection as casual Antidotes against Organophosphate Poisonings and current solutions for auto-injectors," Arh Hig Toksikol 2006, 57:435-443.
International Search Report and Written Opinion of the ISA issued in PCT/US09/35539 dated Jul. 17, 2009 (8 pgs).
International Search Report and Written Opinion of the ISA issued in PCT/US09/52457 dated Oct. 6, 2009 (9 pgs).
Luo et al, "An in Vitro Comparative Study on the Reactivation of Nerve Agent-Inhibited Guinea Pig and Human Acetylcholinesterases by Oximes"; Biochemistry 2007, 46, pp. 11771-11779.

(56) References Cited

OTHER PUBLICATIONS

Garcia et al, "Sensitive and Rapid Blood and Tissue HPLC Oxime Assay and Pharmacokinetics of MMB-4 in Guinea Pigs and African Green Monkeys"; Walter Reed Army Institute of Research, Nov. 1, 2006, (8 pgs).
U.S. Office Action dated Jun. 22, 2011 issued in related U.S. Appl. No. 12/047,988.
U.S. Office Action dated Aug. 15, 2011 issued in related U.S. Appl. No. 11/555,995.
Alyautdin, et al, "Drug delivery to brain by nanoparticles," (2003) eksperimental'naya i Klinicheskaya Farmakologiya, 66 (2), pp. 65-68. English language Abstract can be found on p. 68, final paragraph.
Antonijevic et al., "Unequal Efficacy of Pyridinium Oximes in Acute Organophosphate Poisoning," Clinical Medicine & Research, vol. 5, No. 1:71-82, Mar. 1, 2007.
Luo, et al., "Development of a broad-spectrum Oxime for the treatment of nerve agent toxicity," Conference paper, Division of Biochemistry, Walter Reed Army Institute of Research, Silver Spring, MD 20910, Report Date: Nov. 2006 Report No. A376184. Available at http://www.dtic.mil/cgi-bin/GetTRDoc?Location=U2&doc=GetTRDoc.pdf&AD=ADA481673, retrieved on Mar. 9, 2011.
European Supplementary Search Report—mailing date Sep. 27, 2011, issued in related European appln. No. 09718843.7.
Sevelova et al, "Antidotal Treatment of GF-agent intoxication in mice with bispyridinium Oximes", Toxicology, vol. 207, No. 1, pp. 1-6, 2005.
Aurbek et al, "Analysis of Inhibition, Reactivation and Aging Kinetics of Highly Toxic Organophosphorus Compounds with Human and Pig Acetylcholinesterase", Toxicology, vol. 224, No. 1-2. pp. 91-99, 2006.
U.S. Office Action dated Nov. 1, 2011 issued in related U.S. Appl. No. 11/555,995.
Patani et al, "Bioisosterism: A Rational Approach in Drug Design", (Chemical Reviews, vol. 96, No. 8, pp. 3147-3176; 1996.
Giulian et al, "Short Communication", Optical and Quantum Electronics, vol. 9, pp. 263-264; 1977.
U.S. Office Action dated Mar. 11, 2011 issued in related U.S. Appl. No. 12/245,450.
Office Action dated Dec. 29, 2011 issued in related U.S. Appl. No. 12/047,988.
Office Action dated Nov. 29, 2011 issued in related U.S. Appl. No. 12/245,450.
Wu, et al., "Blood-Brain Barrier Transport of Reduced Folic Acid," Pharm Res. Mar. 1999;16(3):415-9.
Office Action dated Jan. 5, 2012 issued in related U.S. Appl. No. 12/702,095.
European Search Report dated Oct. 31, 2011 issued in related European Patent Application No. 09807064.2.
Bagryanskaya, et al., "Study of alkaloids from the flora of the Siberian and Altai regions. 6.* Crystal and molecular structure of songorine Z-oxime," Russian Chemical Bulletin, International Edition, vol. 50, No. 11, pp. 2092-2094, Nov. 2001.
Gao, et al., "Influence of particle size on transport of methotrexate across blood brain barrier by polysorbate 80-coated polybutylcyanoacrylate nanoparticles," International Journal of Pharmaceutics 310 (2006) 213-219.
Hobbiger, et al., "Reactivation of Phosphorylated Acetocholinesterases by Pyridinium Aldoximes and Related Compounds," Biochem J. May 1960; 75(2): 363-372.
Kuca, et al., "Effective bisquaternary reactivators of tabun-inhibited AChE," J. Appl. ToxiCol. 2005; 25: 491-495.
Liu, et al., "Biologically active core/shell nanoparticles self-assembled from cholesterol-terminated PEG-TAT for drug delivery across the blood-brain barrier," Biomaterials 29 (2008) 1509-1517.
Macauley, et al., Chromatographic separation and NMR characterization of the isomers of MMB-4 a bis-(pyridiniumaldoxime), Journal of Pharmaceutical and Biomedical Analysis 49 (2009) 889-894.

Office Action dated Sep. 14, 2012 issued in related U.S. Appl. No. 12/047,988.
Office Action dated Sep. 27, 2012 issued in related U.S. Appl. No. 12/702,095.
Office Action dated Jan. 20, 2013 issued in related Israeli Patent Application No. 208084.
Gelperina, et al., "Drug delivery to the brain using surfactant-coated poly(lactide-co-glycolide)nanoparticles: Influence of the formulation parameters," European Journal of Pharmaceutics and Biopharmaceutics (2009) doi:10.1016/j.ejpb.2009.09.003.
Kurakhmaeva, et al., "Brain targeting of nerve growth factor using poly(butyl cyanoacrylate) nanoparticles," Journal of Drug Targeting, 2009; 17(8): 564-574.
Hekmatara, et al., "Efficient systemic therapy of rat glioblastoma by nanoparticle-bound doxorubicin is due to antiangiogenic effects," Clinical Neuropathology, vol. 28—No. 3/2009 (153-164).
Zensi, et al., "Albumin nanoparticles targeted with Apo E enter the CNS by transcytosis and are delivered to neurones," Journal of Controlled Release 137 (2009) 78-86.
Ulbrich, et al., "Transferrin- and transferrin-receptor-antibody-modified nanoparticles enable drug delivery across the blood-brain barrier (BBB)," European Journal of Pharmaceutics and Biopharmaceutics 71 (2009) 251-256.
Pereverzeva, et al., "Intravenous tolerance of a nanoparticle-based formulation of doxorubicin in healthy rats," Toxicology Letters 178 (2008) 9-19.
Kreuter, et al., "Use of nanoparticles for cerebral cancer," Tumori: 9-4: 271-277, 2008.
Kreuter, "Nanoparticles—a historical perspective," International Journal of Pharmaceutics 331 (2007) 1-10.
Petri, et al., "Mechanism of Action and Surfactant Influence During Chemotherapy of Brain Tumour Using Doxorubicin-Loaded Poly(butyl Cyanoacrylate) Nanoparticles," NSTI-Nanotech 2007, vol. 2, 2007, p. 386-389.
Ambruosi, et al., "Influence of surfactants, polymer and doxorubicin loading on the anti-tumour effect of poly(butyl cyanoacrylate) nanoparticles in a rat glioma model," Journal of Microencapsulation, Aug. 2006; 23(5): 582-592.
Ambruosi, et al., "Biodistribution of polysorbate 80-coated doxorubicin-loaded [14C]-poly(butyl cyanoacrylate) nanoparticles after intravenous administration to glioblastoma-bearing rats," Journal of Drug Testing, Feb. 2006; 14(2): 97-105.
Ambruosi, et al., "Body distribution of polysorbate-80 and doxorubicin-loaded [14C]-poly(butyl cyanoacrylate) nanoparticles after i.v. administration in rats," Journal of Drug Targeting, Dec. 2005; 13(10): 535-542.
Schuller et al., "Degradation of microvascular brain endothelial cell β-catenin after co-culture with activated neutrophils from patients undergoing cardiac surgery with prolonged cardiopulmonary bypass," Biochemical and Biophysical Research Communications 329 (2005) 616-623.
Kreuter, "Application of nanoparticles for the delivery of drugs to the brain," International Congress Series 1277 (2005) 85-94.
Kreuter, "Influence of the Surface Properties on Nanoparticle-Mediated Transport of Drugs to the Brain," Journal of Nanoscience and Nanotechnology, 2004, vol. 4, No. 5; p. 484-488.
Kreuter, "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles," Pharmaceutical Research, vol. 20, No. 3, Mar. 2003; p. 409-416.
Kreuter, "Transport of Drugs Across the Blood-Brain Barrier by Nanoparticles," Curr. Med. Chem.—Central Nervous System Agents, 2002, 2, 241-249.
Kreuter, et al."Apolipoprotein-medicated Transport of Nanoparticle-bound Drugs Across the Blood-Brain Barrier," Journal of Drug Testing, 2002 vol. 10 (4), pp. 317-325.
Gelperina, et al., "Toxicological studies of doxorubicin bound to polysorbate 80-coated poly(butyl cyanoacrykate) nanoparticles in healthy rats and rats with intracranial glioblastoma," Toxicology Letters 126 (2002) 131-141.
Kreuter, "Nanoparticulate systems for brain delivery of drugs," Advanced Drug Delivery Reviews 47 (2001) 65-81.

(56) References Cited

OTHER PUBLICATIONS

Ramge, et al., "Polysorbate-80 coating enhances uptake of polybutylcyanoacrylate (PBCA)-nanoparticles by human and bovine primary brain capillary endothelial cells," European Journal of Neuroscience, vol. 12, pp. 1931-1940 (2000).

Ramge, et al., "Circadian Phase-dependent Antinociceptive Reaction in Mice and the Tail-flick Test after Intravenous Injection of Dalargin-Loaded Nanoparticles," Chronobiology International, 16(6), 767-777 (1999).

Balali-Mood MD PHD, et al., "Neurotoxic Disorders of Organophosphorous Compounds and Their Managements," Arch Iranian Med 2008; 11 (1): 65-89.

Kuca, et al., "Preparation of Oxime HI-6 (Dichloride and Dimethanesulphonate)—Antidote against Nerve Agents," Defense Science Journal, vol. 58, No. 3, May 2008, pp. 399-404.

Kuca, et al., "In Vitro Reactivation Potency of Acetylcholinesterase Reactivators—K074 and K075—to Reactivate Tabun-inhibited Human Brain Cholinesterases," Neurotoxicity Research, 2007, vol. 11(2), pp. 101-106.

* cited by examiner

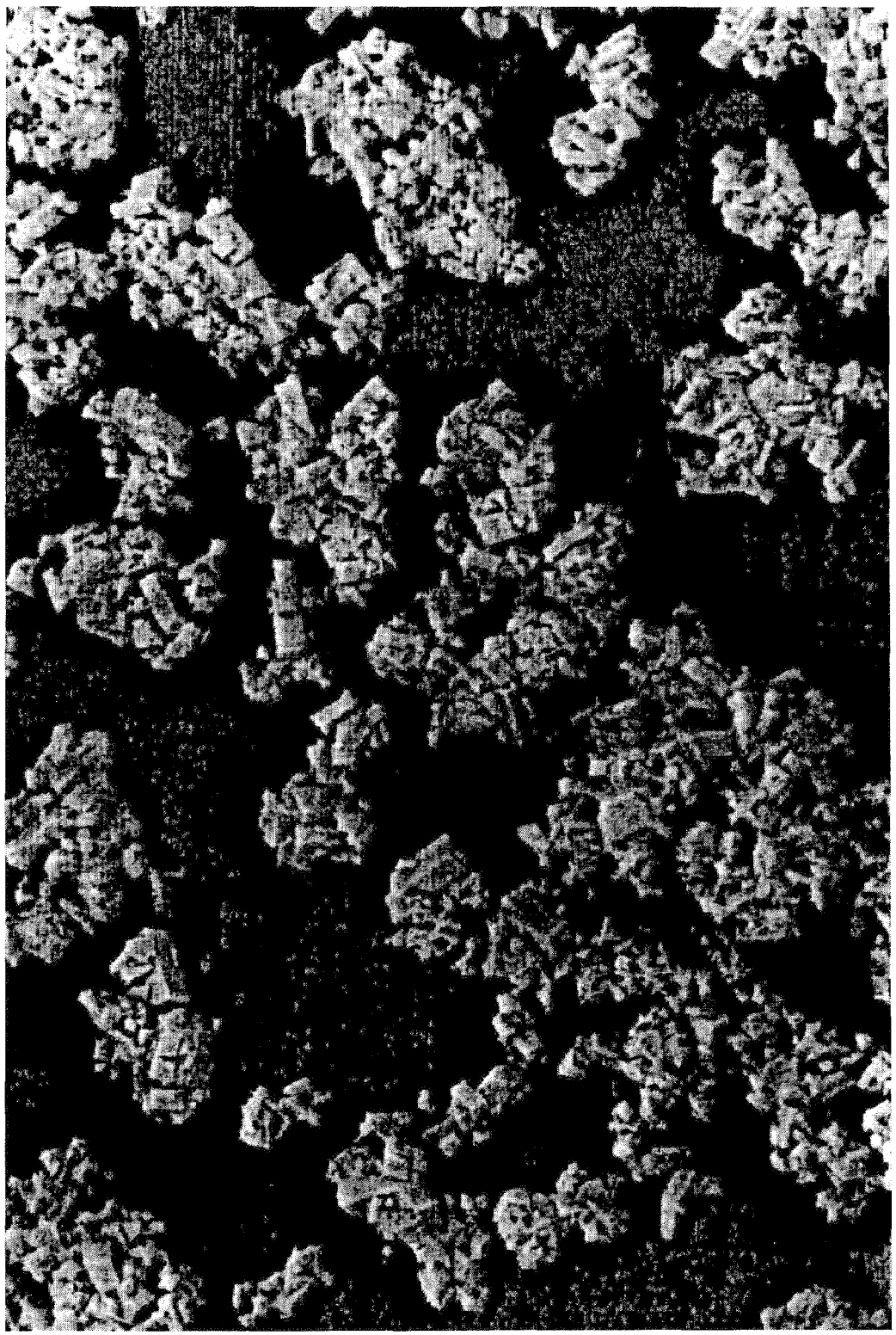

TWO PHASE BIOACTIVE FORMULATIONS OF BIS-QUATERNARY PYRIDINIUM OXIME SULFONATE SALTS

GOVERNMENT RIGHTS CLAUSE

This invention was made with United States Government support under Contract No. W9113M-05-C-0199 awarded by the United States Army. The Government has certain rights in this invention.

FIELD OF THE INVENTION

The present invention relates to two-phase systems of a bioactive ingredient in particle form that has limited or no solubility in a liquid medium, which provides stability to the active ingredient that is similar to the active ingredient when in the solid state. The active ingredient may be a bis-quaternary pyridinium-aldoxime salt which may be used for treatment of exposure to cholinesterase inhibitors, such as a phosphorous containing cholinesterase inhibitor type compounds.

BACKGROUND

Various small bioactive molecules, once formulated, tend to be relatively unstable along with relatively short shelf life and a need for refrigeration. When dissolved in a given liquid, the activity and pharmaceutical effectiveness may be compromised. This problem has been addressed by, e.g., the preparation of freeze-dried formulations along with reconstitution as well as encapsulation and forming a liquid suspension. However, encapsulation may then interfere with in vivo performance where quick release may be desired.

The need for more stable formulations of a bioactive molecule is particular relevant with respect to the on-going need to develop treatment protocols for cholinesterase inhibiting chemicals. That is, stimulating signals are typically carried by acetylcholine within a nervous system synapse. Such signals may be discontinued by a specific type of cholinesterase enzymes, acetylcholinesterase, which breaks down acetylcholine. If cholinesterase inhibiting chemicals are present, they may then prevent the breakdown of acetylcholine thereby disrupting normal nervous system activity. For example, certain chemical classes of pesticides, such as organophosphates and carbamates, may result in toxic cholinesterase inhibition. Accordingly, if an individual is regularly exposed to such inhibitors, there remains a need to therapeutically treat such toxicity. Among other things, individuals or animals who may have been exposed to a carbamate type cholinesterase inhibitor may currently be treated with atropine, and those exposed to organophosphates may beneficially be treated with a pralidoxime antidote.

SUMMARY

In a first exemplary embodiment, the present disclosure relates to a composition comprising a bis-quaternary pyridinium-2-aldoxime salt of the formula:

wherein R1 is a methyl and/or ethyl group wherein the salt is in particle form at a diameter of 1.0 nanometer to 100 microns and the salt is combined in a liquid wherein the solubility of the particle in the liquid is less than or equal to 10% by weight.

In a second exemplary embodiment, the present disclosure relates to a composition comprising a bis-quaternary pyridinium-2-aldoxime salt of the formula:

wherein R1 is a methyl and/or ethyl group wherein the salt is in particle form at a diameter of 1.0 nanometer to 100 microns and the salt is combined in a liquid wherein the solubility of the particle in the liquid is less than or equal to 10% by weight.

In a third exemplary embodiment, the present disclosure is directed at a method for preparing a liquid composition containing particles of a bis-quaternary pyridinium-2-aldoxime salt comprising supplying pyridine-4-aldoximine of the formula:

treating the pyridine-4-aldoximine with diodomethane to form 1,1'-methylenebis[4-[(hydroxyimino)methyl]-pyridinium]diodide of the following formula:

converting the 1,1'-methylenebis[4-[(hydroxyimino)methyl]-pyridinium]diodide to the following structure via ion exchange of the iodine to provide the following bis-quaternary pyridinium-2-aldoxime salt:

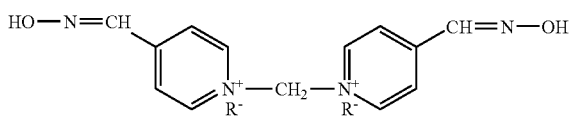

wherein R is a halogen atom or an alkyl sulfonate group and where the alkyl sulfonate is of the general structure:

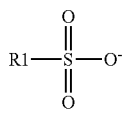

where R1 is a methyl or ethyl group;

wherein the bis-quaternary pyridinium-2-aldoxime salt is formed into particles having a diameter of 1.0 nanometer to 100 microns and combined in a liquid wherein the solubility of the particles in the liquid is less than or equal to 10% by weight.

In yet another exemplary embodiment, the present disclosure relates to a therapeutic method of treating a person or animal for intoxication with a cholinesterase inhibitor, comprising administering to a person or animal a bioactive compound capable of therapeutically treating for the presence of a cholinesterase inhibitor, wherein said bioactive compound is in particle form at a diameter of 1.0 nanometers to 100 microns and combined in a liquid wherein the solubility of said particle in said liquid is less than or equal to 10% by weight.

BRIEF DESCRIPTION OF THE DRAWINGS

FIG. 6A is a scanning electron micrograph of MMB4 DMS Polymorph A.

DETAILED DESCRIPTION

Figure 1:
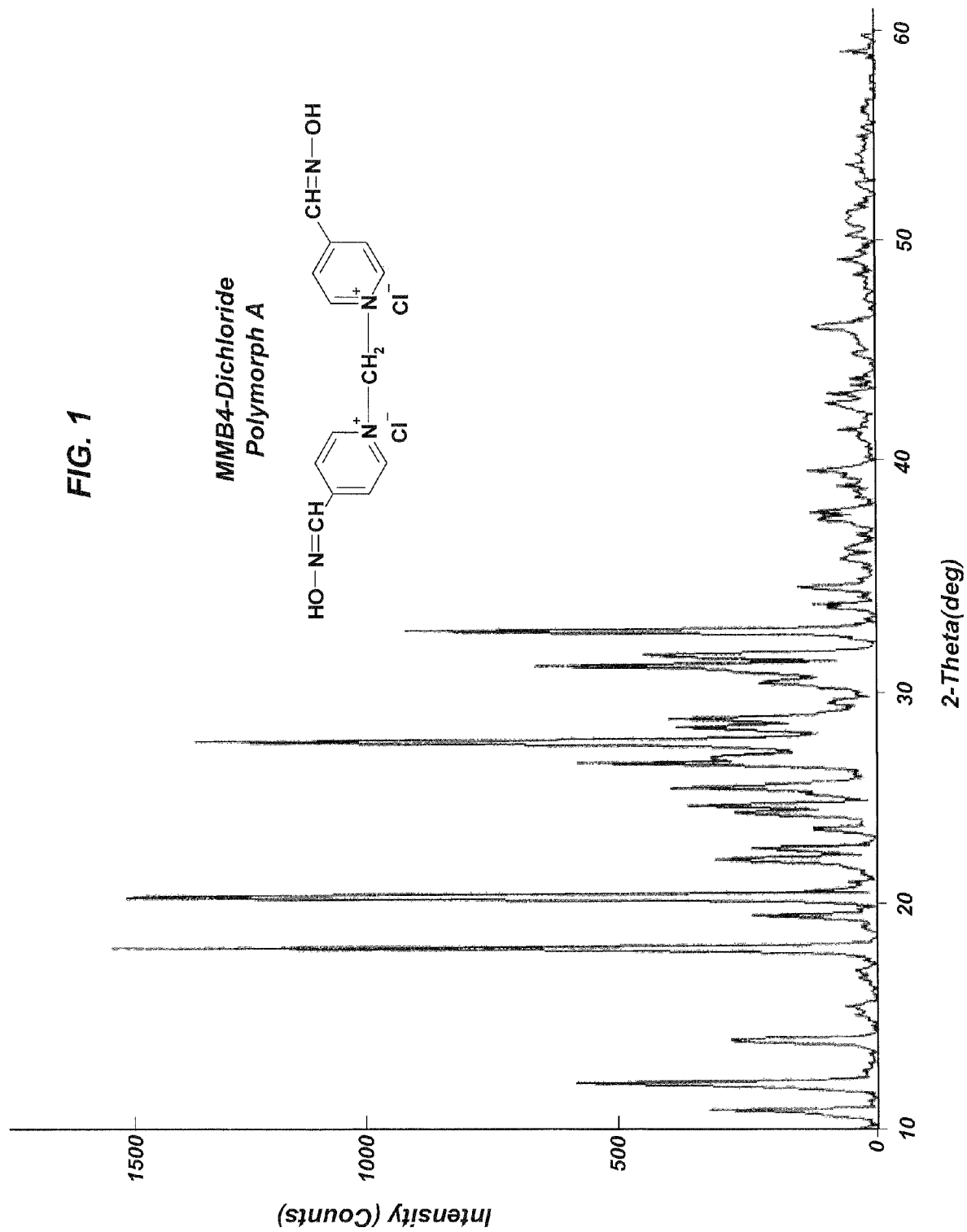
FIG. 1 is an X-ray diffraction pattern for MMB4-Dichloride Polymorph A.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

As alluded to above, the present disclosure is directed at a composition and method for delivery of a bioactive compound where the activity of the compound in the solid state may be preserved. A bioactive compound herein may be understood as a compound having beneficial prophylactic and/or therapeutic properties when administered to an animal or human. The bioactive compound herein may therefore be provided in solid particulate form, wherein the diameter (largest linear dimension through the particle) may be in the range of 1 nanometer (nm) to 100 microns (μm), including all values and increments therein. For example, the particles herein may have a diameter of 1 nm to 100 μm, or a diameter of 10 μm to 100 μm, or 1 μm to 10 μm.

The above referenced bioactive particulate compound may be combined in a liquid medium, where the solubility of the particulate in the liquid medium is regulated to maintain the stability and bioactivity of the particulate. Accordingly, a substantially two phase (solid-liquid) system is provided. That is, the solubility of the particulate may be up to and including 10.0% by weight, including all values and increments in the range of 0.01% (wt.) to 10.0% (wt). More specifically, the solubility may be in the range of 0.01% (wt.) to 1.00% (wt.), or in the range of 0.00% (wt.) to 0.05% (wt.). As may therefore now be appreciated, the solubility of the particulate in the liquid medium herein may amount to that situation where the particulate is completely insoluble.

Suitable liquids for the bioactive particulate herein may therefore be those liquids that provide the limited and/or even zero levels of solubility noted above. In particular, the liquids herein may include fluorinated hydrocarbon liquids, which may be understood as liquids that include a carbon-fluorine (C—F) bond. In particular, the liquid may therefore include perfluorodecaline ($C_{10}F_{18}$). The liquids herein may also include vegetable oils, which may be understood as those oils that are extracted from plants or which are synthesized to provide a chemical composition that resembles an extracted oil. For example, the liquids herein may include one or more edible oils, such as cottonseed oil, soybean oil and/or sesame oil. Moreover, the liquids herein may include organic liquids, such as an organic alcohol, e.g., ethyl alcohol. With respect to the various liquids noted above, it is also worth noting that the liquids may be selected such that the liquids themselves are also biocompatible when utilized as a carrier for the bioactive particulate. Reference to biocompatible liquid may therefore be understood as a liquid which does not trigger any toxic or injurious effect on the biological system for which it is delivered. Furthermore, it should be appreciated that the above referenced liquids may be combined, e.g., one may utilize a mixture of an organic alcohol and a vegetable oil, which may therefore define a mixture of ethyl alcohol with cottonseed oil, soybean oil and/or sesame oil.

The amount of bioactive particulate with limited or zero solubility in the above referenced liquids may also be controlled. For example, the bioactive particulate may be combined with the liquid such that the bioactive particulate is present at a solids level of 0.01% by weight to 80.00% by weight, including all values and increments therein, in 0.01% increments. For example, the bioactive particulate may be present at a level of 10.00% (wt.) to 50.00% (wt.) with respect to a given liquid. Accordingly, it may be appreciated that for a given combination of bioactive particulate, having, e.g. a diameter of 1 nm to 100 μm, combined with a liquid, where the bioactive particulate has a solubility in the liquid of 0.00% (wt.) to 10.0% (wt.), the bioactive material may be present at a level of up to 80.00% by weight with the liquid being present at a level of 20.00% by weight. Such a formulation of bioactive particulate and liquid may therefore contain relatively high loadings of the bioactive particulate, and as noted above, with a stability and activity that resembles, as noted more fully below, neat solid particulate material. In addition, the formulations of bioactive particulate may include surfactants, which surfactants may be ionic or non-ionic type compounds that may provide improved suspension of the relatively insoluble bioactive particulate in the selected liquid medium. Such surfactants may be present herein at a level of 0.01% to 20.00% by weight.

By way of representative example, bioactive particulate suitable for use herein relates to particulate of certain bis-quaternary pyridinium aldoxime salts. The bioactive particulate may also include their derivatives, such as HI-6 salts, e.g. [(1-(2-hydro-xyiminomethylpyridinium)-3-(4-carbamoylpyridinium)-2-oxapropane dichloride)] and/or Hlo-7 salts, e.g. 1-[[[4-(aminocarbonyl)pyridinio]methoxy]methyl]-2,4-bis[(hydroxyimino)methyl]pyridinium-diiodide. Such bioactive particulate may be used to therapeutically treat intoxication in a person or animal due to the presence of a cholinesterase inhibitor, such as a phosphorous containing cholinesterase inhibitor. It is therefore worth pointing out that organophosphates (OPs) may act as hemi-substrates of cholinesterase by specifically phosphorylating the active site serine. As the rate of hydrolysis of the phosphoryl or phosphonyl enzyme may be relatively slower than deacylation of acytylcholine, OPs are effectively irreversible cholinesterase inhibitors. OPs have also been developed as chemical weapon systems, and relatively potent insecticides, due to their inhibition of the insects' flight muscle cholinesterase, with resulting paralysis and death. It may therefore be appreciated that intoxication by anti-cholinesterase compounds may develop following accidental exposure to organophosphorus insecticides and/or other associated chemical agents. Furthermore, the overall pharmacologic effect of anti-cholinesterases may be due to the inhibition of cholinesterase enzymes throughout the body.

Accordingly, the present disclosure has recognized that one may now provide an improved method for treating a person or animal for intoxication with a cholinesterase inhibitor (i.e. compounds that disrupt the mechanism of nerve transfer) by administering to a person or animal a bioactive compound capable of therapeutically treating for the presence of a cholinesterase inhibitor. The bioactive compound is now advantageously provided as a particle combined a liquid medium, wherein the particle has the above referenced limited solubility, such that liquid formulation provides stability and a therapeutic effect that is commensurate with use of the particle in solid form. Such bioactive compounds suitable for treating for the presence of a cholinesterase inhibitor may include, e.g., atropine and related anticholinergic drugs, as well as the various MMB4 salts disclosed herein.

In a first exemplary embodiment, the present disclosure relates to the preparation of bioactive particulate, as noted above, of a 1,1'-methylenebis[4-(hydroxyimino)methyl]-pyridinium salt, which may be represented by the following general formula:

$$HO-N=CH-\underset{R^-}{\overset{N^+}{\bigcirc}}-CH_2-\underset{R^-}{\overset{N^+}{\bigcirc}}-CH=N-OH$$

where R may be a halide counteranion such as a halogen (e.g. Cl⁻ or Br⁻ or I⁻) in which case the compound may be referred to as "MMB4 Dihalide.". More generally, R may be derived from a salt of an inorganic or organic acid. For example, the anion may be derived from hydrogen sulfate ($H_2SO_4$), nitrate, fumarate, lactate, tartate, citrate, and/or acetate.

In addition, R may be a counteranion such as an alkyl sulfonate group. In such a case, the 1,1'-methylenebis[4-(hydroxyimino)methyl]-pyridinium salt would assume the following general formula:

$$HO-N=CH-\overset{N^+}{\bigcirc}-CH_2-\overset{N^+}{\bigcirc}-CH=N-OH$$

$$R1-\overset{O}{\underset{O}{\overset{\|}{S}}}-O^- \qquad O^--\overset{O}{\underset{O}{\overset{\|}{S}}}-R1$$

wherein R1 may be selected such that it does not interfere (e.g. steric interference) with the formation of the particular polymorphic pyridinium salts noted below. Accordingly, R1 may be a methyl (—$CH_3$) group, and it is contemplated herein that it may also include ethyl type group functionality (—$CH_2CH_3$).

One particularly useful and convenient synthetic procedure for the formation of the pyridinium salts of the present disclosure may involve the preparation of 1,1'-methylenebis[4-[(hydroxyimino)methyl]-pyridinium]diodide hereinafter referred to as "MMB4 DI", which may then be converted to 1,1'-methylenebis[4-[(hydroxyimino)methyl]-pyridinium] dimethanesulfonate "MMB4 DMS." This synthetic procedure is outlined in the general reaction scheme illustrated below:

Pyridine-4-aldoxime $\xrightarrow{\underset{CH_3CN}{CH_2I_2}}$ MMB4 DI

↓ Methanesulfonate ion exchange resin

-continued

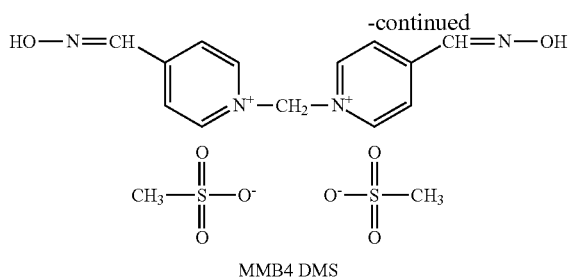

MMB4 DMS

In addition, it may be appreciated that the MMB4 DI may be converted, again by the convenient procedure of ion exchange, to a particular dihalide salt, such as the dichloride salt, as illustrated below:

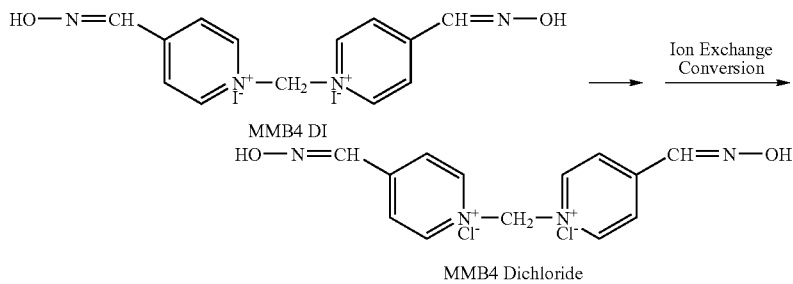

It has been determined that the MMB4 dichloride and/or the MMB4 DMS compounds noted above may be isolated in one of two polymorphic forms, as disclosed herein, by control of, e.g., the solvents that may be employed for the pyridinium salt recrystallization. In addition, such polymorphic forms, as also noted above, provided the ability to offer improved prophylactic or therapeutic treatment of a person or animal intoxicated with a cholinesterase inhibitor. Accordingly, attention is therefore next directed to FIG. 1, which provides the x-ray diffraction pattern [intensity (counts) versus 2-Theta(degrees)] for the MMB4 dichloride compound in the form of what may now be termed MMB4-dichloride Polymorph A. The diffraction patterns (as well as the other diffraction patterns reported herein) were made on a Siemens Kristalloflex 805 with a model D500 goniometer, serial number WM80030464X. The diffraction patterns were then processed using JADE v3.1 from Materials Data, Inc (program serial number MDI-R95704. In general, a representative portion of the sample for analysis was ground to a grain size of less than 25 microns and then spread on a polycarbonate specimen holder. The x-ray tube was run at 40 kV and 30 mA with a 2-theta range of 10-60 degrees. The instrument may be calibrated at regular intervals using appropriate standards.

As can be seen from FIG. 1, the MMB4 dichloride compound in the form of polymorph A herein indicates one or more x-ray diffraction peaks with relative intensity counts (artificial units) between 500-1500 at the 2 Theta angles of between 10-35 degrees, which relatively intensity counts for the peaks drop to a level of less than 500 counts at 2 Theta angles of greater than about 35 degrees. That is, no peaks are present with relative intensity counts of more than 250 at 2 Theta angles between 35-60 degrees. Accordingly, it may be understood herein that the MMB4 dichloride compound in the form of polymorph A may be characterized as having an x-ray diffraction pattern with distinguishing peaks at the 2 Theta angles of between 10-35 degrees as compared to the non-distinguishing x-ray diffraction peaks at the 2 Theta angles of greater than 35 degrees. By reference to distinguishing peaks, it may be understood (upon consideration of FIG. 1) as those peaks and/or collection of peaks within the 2 Theta angles of 10-35 degrees which then may be employed to provide identifiable d-spacing (Braggs Law) for the MMB4 dichloride polymorph A. Accordingly, reference to a collection of peaks herein may include, e.g. information sourced from 2-100 peaks, including all values and increments within the range of 2-100.

Figure 2:
FIG. 2 is a scanning electron micrograph of MMB4 Dichloride Polymorph A.

Attention is therefore next directed to FIG. 2, which provides a scanning electron micrograph of MMB4 dichloride Polymorph A. As can be seen, MMB4 dichloride Polymorph A may also be characterized as having a needle-like particulate structure, with an aspect ratio (AR) or length divided by largest diameter of greater than 2:1. More particularly, the aspect ratio may be in the range of 2:1 to 16:1, including all values and increments therein.

Figure 3:
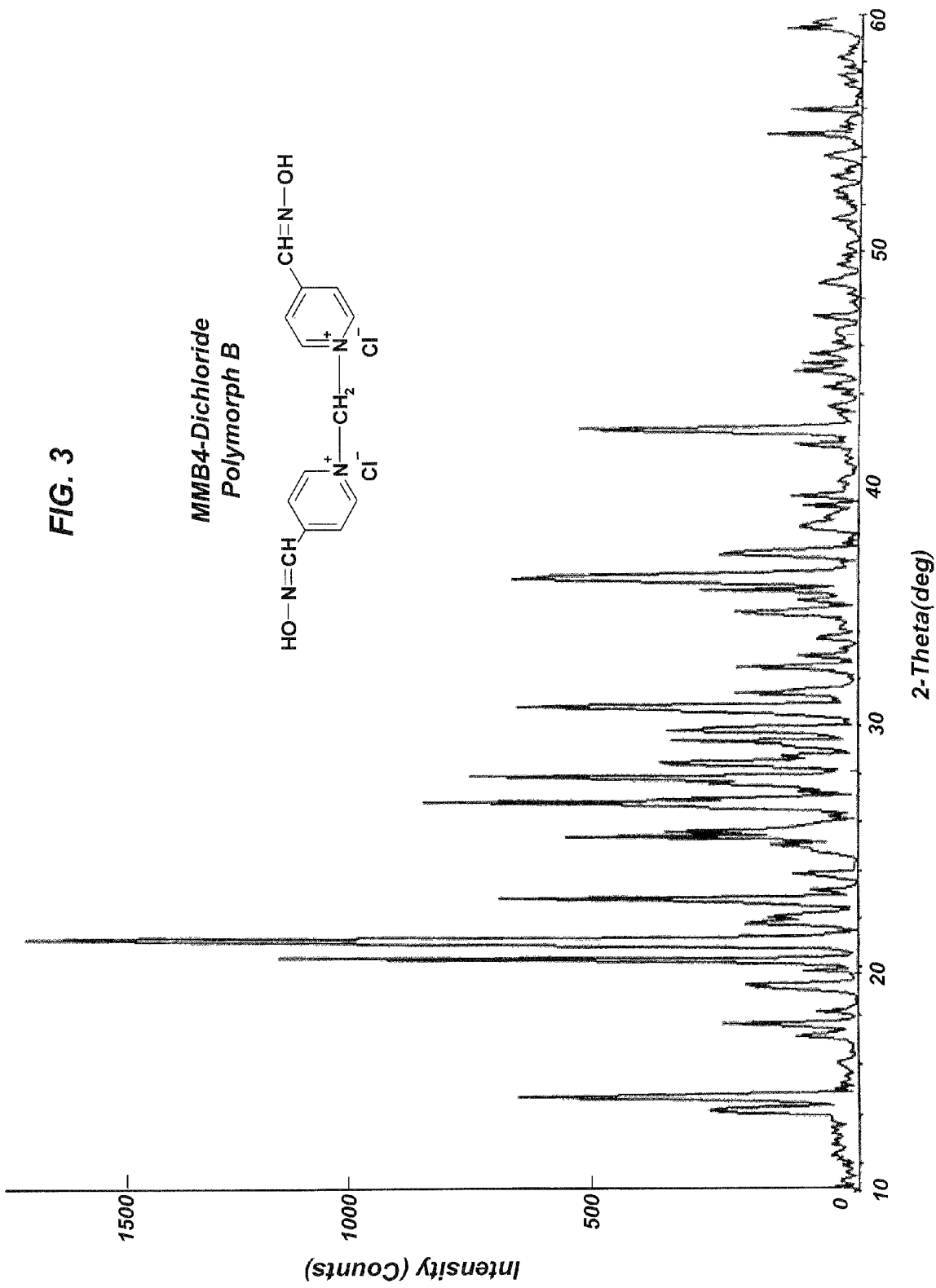
FIG. 3 is an X-ray diffraction pattern for MMB4 Dichloride Polymorph B.

Attention is next directed to FIG. 3, which provides the x-ray diffraction pattern of MMB4 dichloride Polymorph B. As can be seen, MMB4 dichloride Polymorph B indicates one or more x-ray diffraction peaks having relative intensity counts (artificial units) between 500-1500 at the 2 Theta angles of between 10-45 degrees, which relatively intensity counts for the peaks drop to a level of less than 500 counts at 2 Theta angles greater than about 45 degrees. That is, no peaks are present with relative intensity counts of more than 250 at 2 Theta angles between 45-60 degrees. Accordingly, it may be understood herein that the MMB4 dichloride compound in the form of polymorph B may be characterized as having an x-ray diffraction pattern with distinguishing peaks at the 2 Theta angles of between 10-45 degrees as compared to the non-distinguishing x-ray diffraction peaks at the 2 Theta angles of greater than 45 degrees. By reference to distinguishing peaks, it may again be understood (upon consideration of FIG. 3) as those peaks and/or collection of peaks within the 2 Theta angles of 10-45 degrees which then may be employed to provide identifiable d-spacing (Braggs Law) for the MMB4 dichloride polymorph B.

Figure 4:
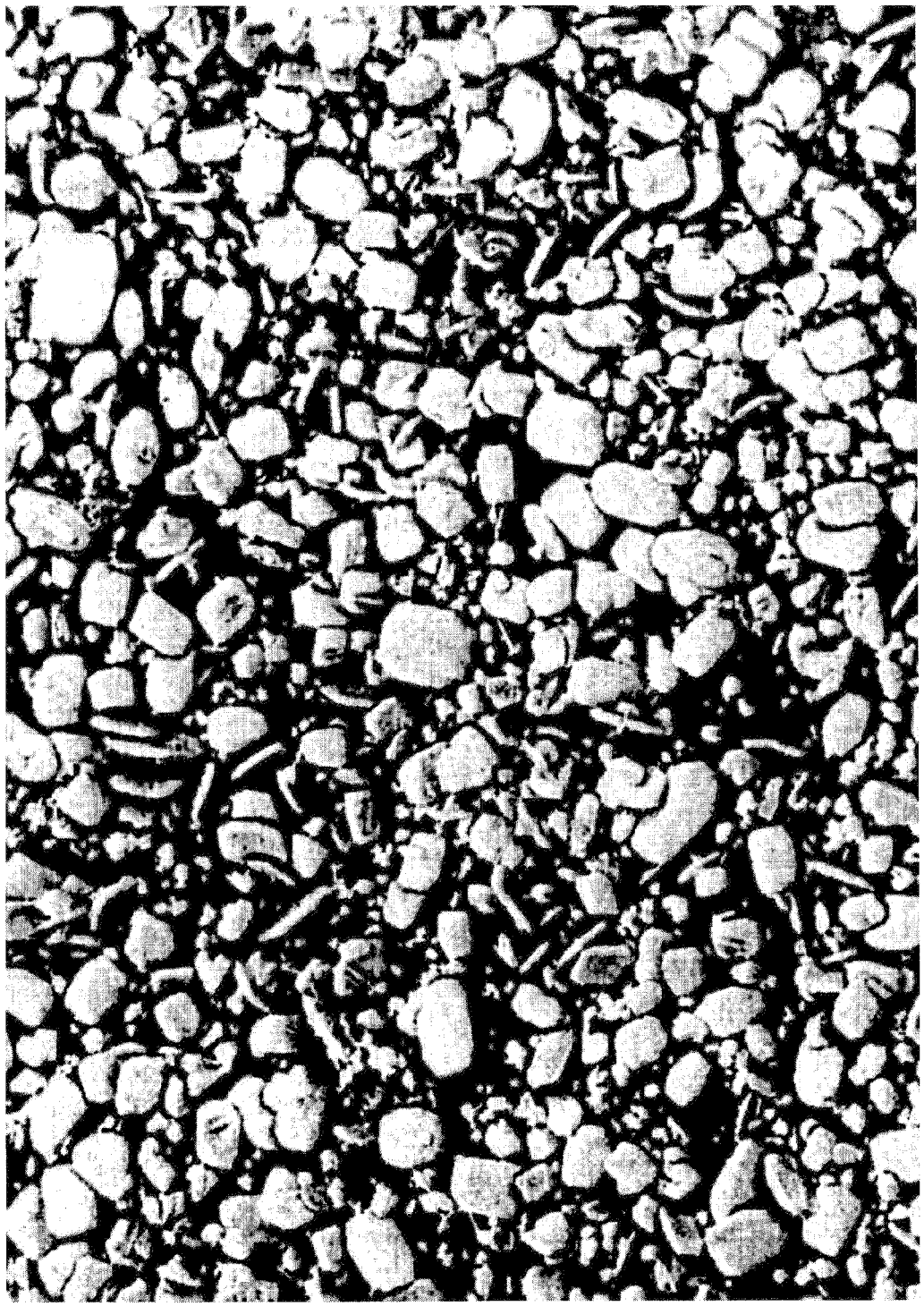
FIG. 4 is a scanning electron micrograph of MMB4 Dichloride Polymorph B/

Attention is therefore next directed to FIG. 4 which provides a scanning electron micrograph of MMB4 dichloride Polymorph B. As can be seen, MMB4 dichloride Polymorph B may also be characterized as having either a particulate structure that is of a square, rectangular, rhomboid (i.e. a parallelogram in which adjacent sides are of unequal lengths) and/or rhombus (a rhomboid with right angled corners) type geometry.

Figure 5:
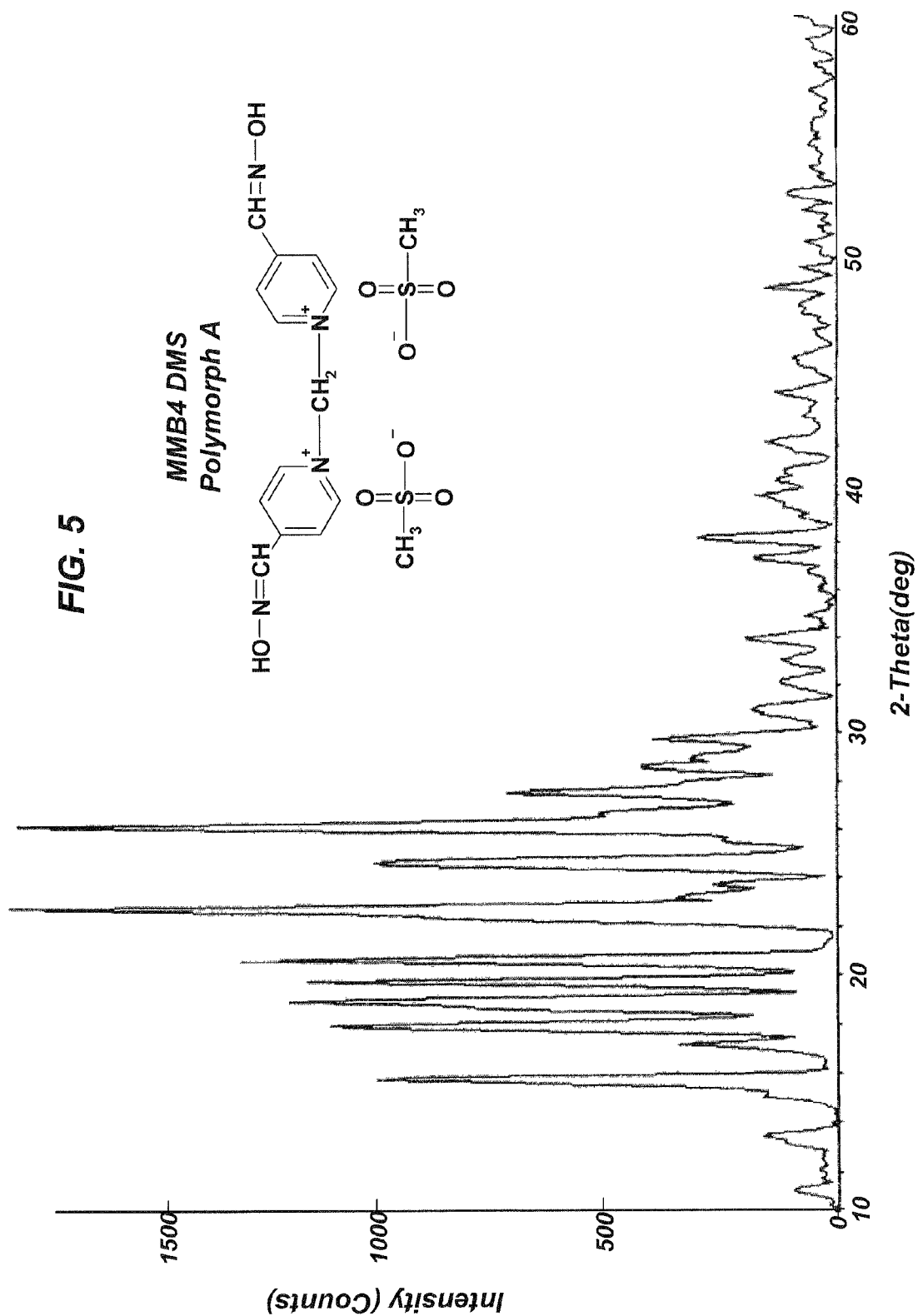
FIG. 5 is an X-ray diffraction pattern for MMB4 DMS Polymorph A.

Attention is next directed to FIG. 5 which provides the x-ray diffraction pattern of MMB4 DMS Polymorph A. As can be seen, MMB4 DMS Polymorph A indicates one or more x-ray diffraction peaks with relative intensity counts (artificial units) between 500-1500 at the 2 Theta angles of between 10-30 degrees, which relatively intensity counts for the peaks drop to a level of less than 500 counts at 2 Theta angles greater than about 30 degrees. That is, no peaks are present with relative intensity counts of more than 250 at 2 Theta angles between 30-60 degrees. Accordingly, it may be understood herein that the MMB4 DMS compound in the form of Polymorph A may be characterized as having an x-ray diffraction pattern with distinguishing peaks at the 2 Theta angles of between 10-30 degrees as compared to the non-distinguishing x-ray peaks at the 2 Theta angles in the range of greater than 30 degrees, e.g. in the range of greater than 30 degrees to about 60 degrees. By reference to distinguishing peaks, it may again be understood (upon consideration of FIG. 5) as those peaks and/or collection of peaks within the 2 Theta angles of 10-30 degrees which then may be employed to provide identifiable d-spacing (Braggs Law) for the MMB4 DMS Polymorph A.

Figure 6B:
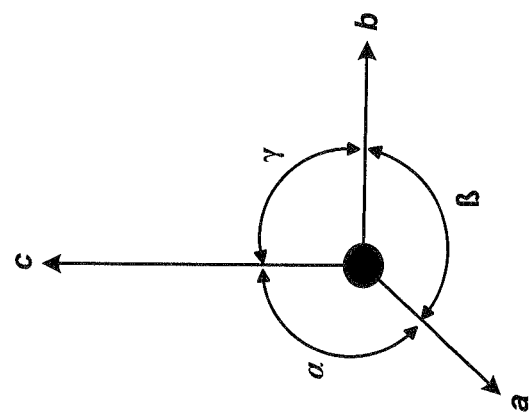
FIG. 6B is an illustration of the crystalline structure of MMB4 DMS Polymorph A identified in FIG. 6A.
Figure 6B:
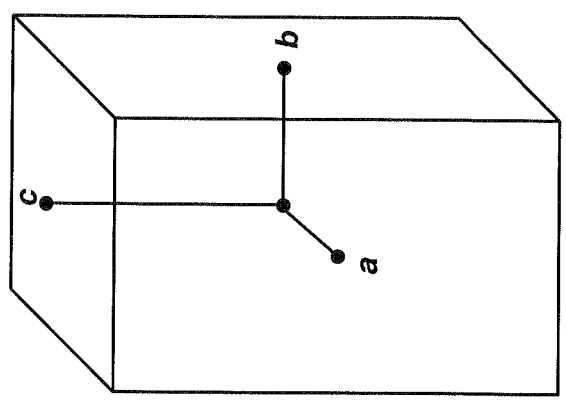

FIG. 6A next provides a scanning electron micrograph of MMB4 DMS Polymorph A. As can be seen, MMB4 DMS Polymorph A may be described as having cubic rectangular type crystal structure or geometry. A cubic rectangular geometry may be understood as a cubic configuration that may be stretched along its (c) axis to provide a rectangular configuration, consisting of three substantially equal or equatorial (a, b and c) axes at 90° (+/−5°) and the c axis is longer than the horizontal axis. See FIG. 6B and angles α, β, and γ which are at 90° (+/−5°).

Figure 7:
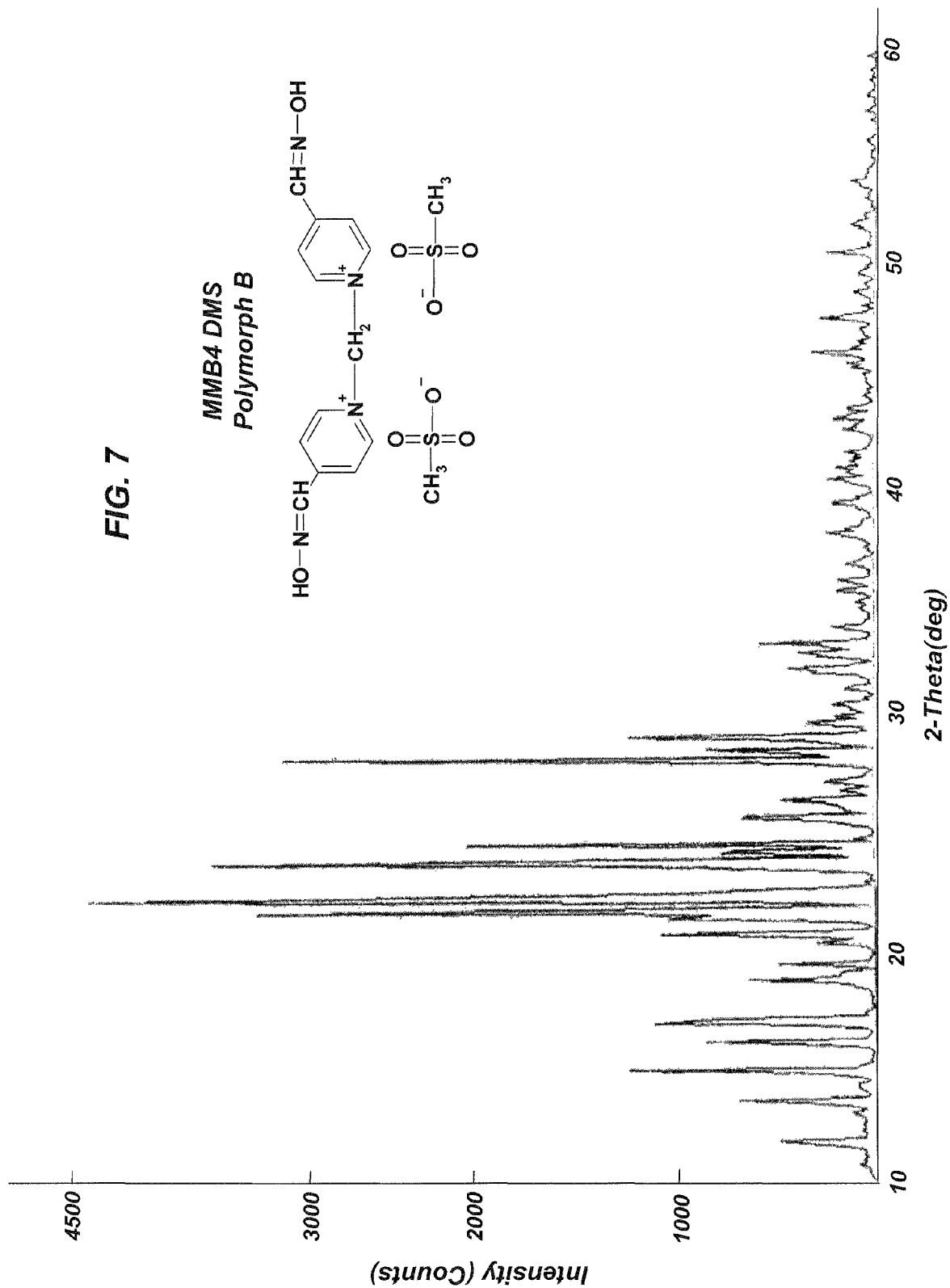
FIG. 7 is an X-ray diffraction pattern for MMB4 DMS Polymorph B.

Attention is next directed to FIG. 7 which provides the x-ray diffraction pattern of MMB4 DMS polymorph B. As can be seen, MMB4 DMS Polymorph B indicates one or more x-ray diffraction peaks with relative intensity counts (artificial units) between 1000-4500 at the 2 Theta angles of between 10-30 degrees, which relatively intensity counts for the peaks drop to a level of less than 500 counts at 2 Theta angles greater than about 30 degrees. That is, no peaks are present with relative intensity counts of more than 500 at 2 Theta angles between 30-60 degrees. Accordingly, it may be understood herein that the MMB4 DMS compound in the form of polymorph B may be characterized as having an x-ray diffraction pattern with distinguishing peaks at the 2 Theta angles of between 10-30 degrees as compared to the non-distinguishing x-ray diffraction peaks at the 2 Theta angles of greater than 30 degrees. By reference to distinguishing peaks, it may again be understood (upon consideration of FIG. 7) as those peaks and/or collection of peaks within the 2 Theta angles of 10-30 degrees which then may be employed to provide identifiable d-spacing (Braggs Law) for the MMB4 DMS polymorph B.

Figure 8A:
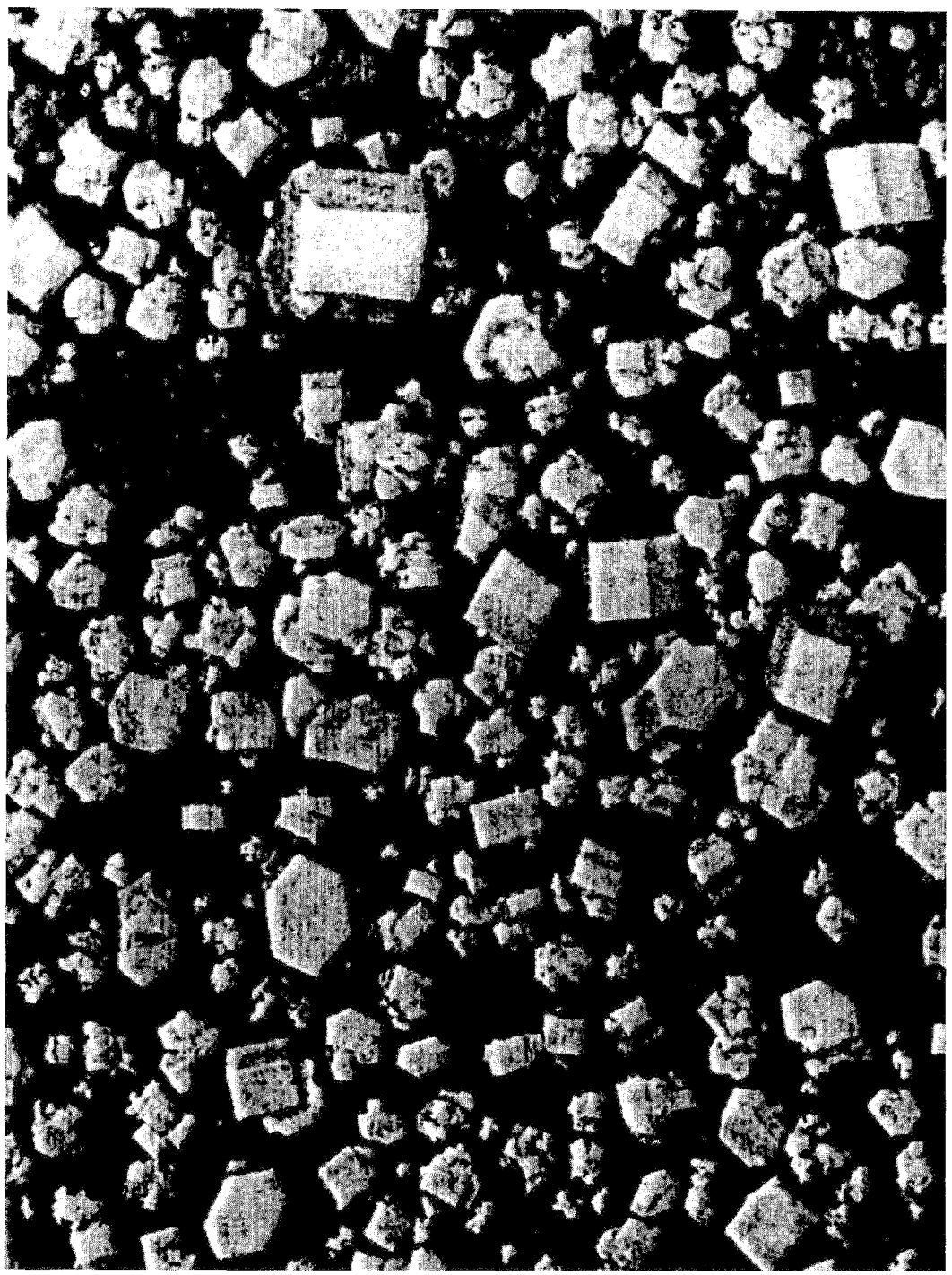
FIG. 8A is a scanning electron micrograph of MMB4 DMS Polymorph B.
Figure 8B:
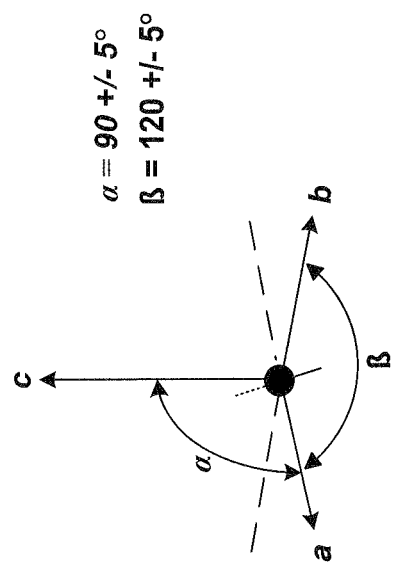
FIG. 8B is an illustration of the crystalline structure of MMB4 DMS Polymorph B identified in FIG. 8A.
Figure 8B:
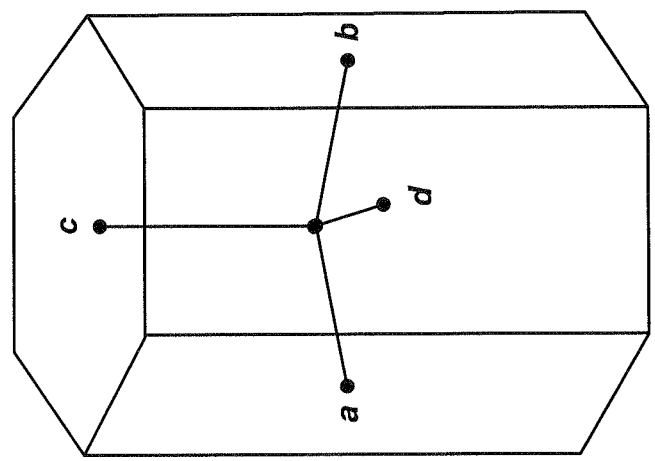

FIG. 8A next provides a scanning electron micrograph of MMB4 DMS Polymorph B. As can be seen, MMB4 DMS Polymorph B may be described as having primarily hexagonal structure. A hexagonal crystal structure may be understood as having four crystallographic axes consisting of three substantially equal or equatorial (a, b, and d) axes at 120° (+/−5°) and one vertical (c) axis that is 90° (+/−5°) to the other three. See, e.g., FIG. 8B, wherein angle α is shown being equal to 120° (+/−5°) and angle β being equal to 90° (+/−5°). The (c) axis may be shorter or longer than the horizontal axis.

Once prepared, the 1,1'-methylenebis-quaternary pyridinium-4-aldoximine compounds, either in the form of polymorph A and/or polymorph B, may be readily formed into particulate form, with diameters of 1 nm to 100 μm, and as noted above, combined with a liquid where the solubility of the particulate is in the range of 0.0% (wt.) to 10.0% (wt.). Such formulations may then be administered in an antidotal amount to therapeutically treat exposure to a phosphorous containing cholesterase inhibitor. Such formulations may therefore amount to liquid suspensions and may be adjusted to have a pH of 1.0 to 5.0, including all values and increments therein. It may also now be appreciated, however, that specific doses may depend on a variety of factors, for example, the age, body weight, general state of health and time of administration and the time and severity of exposure. It is worth noting that parenteral administration may be utilized herein, whether for prophylaxis or therapeutically (i.e., before exposure to a cholinesterase inhibitor).

In addition, the bioactive particulate of relatively low solubility herein in a given liquid medium may include other diluents suitable for preparing an oral pharmaceutical suspension. For example, an oral pharmaceutical suspension of the present invention (bioactive particulate of limited solubility in a given liquid) may include, if necessary, pharmaceutically acceptable additives including auxiliary substances, stabilizing agents, suspending agents, surface tension modifiers, viscosity modifiers, colorants, preservatives, flavoring agents and other commonly used additives such as lactose, citric acid, tartaric acid, stearic acid, magnesium stearate, sucrose, and the like.

The present disclosure may therefore now be considered with respect to the following various non-limiting examples.

Example 1

Preparation of MMB4 Dimethane Sulfonate (Laboratory Scale)

(1) Production of MMB4 Diiodide

To 21.53 g (0.176 mol) of pyridine-4-aldoxime in 250 mL of acetonitrile was added 27.21 g (0.176 mol) of diiodomethane. The reaction mixture was refluxed under argon for 90 hours. The mixture was cooled, filtered and the filter cake washed with 100 ml of acetonitrile. The filter cake was air dried for 30 minutes to yield 41.52 g. The cake was dried under high vacuum to give 41.02 g (91% yield).

(2) Dimethanesulfonate Resin Preparation

In a 250 mL beaker, 30 g of Dowex 550A (OH form), available from the Dow Chemical Company, was added to 84 mL of 10% (v/v) methanesulfonic acid in methanol. The resin was stirred at room temperature for 2 h then filtered through a 150 mL sintered funnel. The resin bed was washed with 2×84 mL portions of methanol and then air-dried for 30 minutes. Total resin weight: 17.6 g, divided into 2×8.8 g portions.

(3) Conversion of MMB4 Diiodide to MMB4 Dimethanesulfonate

A sample of 2.0 g (3.9 mmol) of MMB4 diiodide was dissolved in 100 mL of methanol with stirring in a 50° C. water bath. The solution was cooled to room temperature, then 8.8 g of the mesylate form of Dowex 550A was added and stirred at room temperature for 2 hours. The mixture was filtered through a sintered funnel, washing the resin bed with 10 mL of methanol. An additional 8.8 g of the mesylate form of Dowex 550A was added to the filtrate and the mixture stirred for an additional 2 h. The mixture was filtered and the resin bed washed with 10 mL of methanol.

The filtrate was concentrated to 10 mL, then 35 mL of denatured ethanol (denatured with 5% isopropanol and 5% methanol) was added. The mixture was heated to 50° C. with stirring until complete dissolution (30 min). The solution was allowed to stand for 16 hours at ambient temperature with slow stirring. The mother liquor was decanted and the solids rinsed with 2×5 mL of cold (5° C.) denatured ethanol. The solid was dried at 23 mm Hg and room temperature to yield 1.35 g (77%) of a tan-amber solid (Polymorph A).

Example 2

Preparation Of MMB4 Dimethanesulfonate (Production Scale)

(1) Production of MMB4 Diiodide

A 100-gallon (380 L) reactor is charged with 21.9 kg (179 moles) of pyridine-4-aldoxime and 170 kg of acetonitrile, followed by 48.3 kg (180 moles) of diiodomethane and 37.5 kg of acetonitrile. The mixture is brought to a gentle reflux (approximately 84° C.) with vigorous mechanical stirring under an inert atmosphere (nitrogen). After 72 hours, the mixture is cooled to 40-45° C. with stirring over 5 hours. The resulting suspension is filtered and then washed three times with 25 kg portions of 40-45° C. acetonitrile. The washed filter cake is transferred to drying trays and dried under vacuum with heating 40-45° C. over eight hours. This process yields approximately 37.5 kg (82%) of MMB4 diiodide.

(2) Dimethanesulfonate Resin Preparation

In a 100-gallon (380 L) reactor, 172 kg of methanol is slowly charged to methanesulfonic acid (35.7 kg), maintaining the temperature at 20-40° C. This solution is subsequently added to 77.5 kg of Dowex 550A (OH form), maintaining the temperature below 50° C. The resultant resin/methanol/methanesulfonic acid slurry is then stirred at 25±5° C. for 2-2.5 hours and then filtered. The resin is washed in a plug flow manner with two-153 kg portions of methanol. A final wash of 35 kg of methanol is used to test for residual water; the in-process limit is no more than 0.4%.

(3) Conversion of MMB4 Diiodide to MMB4 Dimethanesulfonate

In a 100-gallon (380 L) reactor, MMB4 diiodide, 10.3 kg, is dissolved in 204.5 kg of methanol with stirring by warming to 50±3° C. for 1-1.5 hours. While maintaining the temperature, half of the previously formed dimethanesulfonate resin is added and stirred at 50±3° C. for 2 to 2.5 hours. The solution is then filtered and the resin is washed with 20.5 kg of methanol. The filtrate and wash are combined and treated as described above with the remaining half of the resin.

After the final filtration and washing, an in-process test is used to monitor iodide concentration. The wash and filtrate are combined and then reduced to a volume of 65-70 L under vacuum at a temperature less than 25° C. After concentrating, 5.5 kg each of isopropanol and methanol are added followed by 98 kg of ethanol. The mixture is heated to reflux (approximately 72° C.) for 1-1.5 hour to achieve complete dissolution.

Once clarity is achieved, the mixture is allowed to cool to 20±5° C. over approximately 9 hours to crystallize, followed by an additional hold time of 7-7.5 hours. The MMB4 dimesylate is then filtered and washed with a mixture of 4.5 kg ethanol and 2.3 kg of methanol. The filter cake is then dried at ambient temperature under vacuum for 8 hours. The typical yield is 5-5.7 kg or 55-63% of MMB4 dimethanesulfonate (Polymorph B).

Example 3

A representative pharmaceutical formulation for MMB4 DMS is set forth below:

450 mg/mL of MMB4 DMS and 5 mg/mL of benzyl alcohol in WFI is adjusted with an acetic acid solution to a pH of about 2.3. The following were then transferred to a 5 mL volumetric flask: 25 mg benzyl alcohol (BA), 1.0 g "0.3% Acetic acid solution" and 2.25 g MMB4 DMS. At this point, WFI water is added to dissolve the solids completely. The pH is then measured and adjusted with acetic acid solution to a pH of about 2.3. At this point one brings the total volume to 5 mL with WFI water. This is then followed by filtering through a 0.2-micron syringe filter.

Example 4

MMB4 DMS Stability In Single-Phase Liquid

As a first initial comparative example MMB4 DMS dissolved as a single phase in an aqueous formulation may degrade primarily to pyridine-4-aldoxime (4-PA), which may therefore be tracked as a marker for stability. Table 1 below therefore provides an indication of the formation of 4-PA from the indicated liquids when the MMB4 DMS As can be seen, the single phase liquids indicated at a minimum the formation of 0.32% by weight 4-PA after one month at 40° C., which projected to a level of 7.5% (wt.)-25% (wt.) at 12 months. This data may then be used as a baseline for evaluation stability of the bioactive/liquid formulations noted herein, where the bioactive particulate, as noted, as limited or zero solubility.

TABLE 1

4-PA Concentration (%) in 800 mg/mL MMB4 DMS With Indicated Liquids

| 40° C. Stability Formulation | Weeks | | | | |
|---|---|---|---|---|---|
| | 0 | 1 | 2 | 4 | 8 |
| Saline | 0.01 | 0.17 | 0.36 | 0.74 | — |
| Saline/5 mg/mL BzOH | 0.01 | 0.16 | 0.35 | 0.66 | — |
| WFI/5 mg/mL BzOH | 0.01 | 0.16 | 0.35 | 0.74 | — |
| WFI/5 mg/mL BzOH @ 2.3 pH MSA | 0.01 | 0.07 | 0.13 | 0.32 | 0.89 |
| WFI/5 mg/mL BzOH @ 2.3 pH HCl | 0.01 | 0.07 | 0.15 | 0.38 | 1.01 |
| WFI/5 mg/mL BzOH @ 3.0 pH MSA | 0.01 | 0.14 | 0.30 | 1.02 | — |

WFI—water for injection.
BzOH—benzyl alcohol.
MSA—methanesulfonic acid.
HCl—hydrochloric acid.

As a further comparative example, MMB4-DMS in solid form was also evaluated for stability, by similarly monitoring the generation of 4-PA. As shown below in Table 2, solid MMB4-DMS was evaluated for stability over a one year time period, at a temperature of 40° C. The level of 4-PA remained at or below 0.04% by weight.

TABLE 2

Stability of Solid MMB4-DMS At 40° C.

| Time (Months) | 4-Pyridine-aldoxime (% by wt.) |
|---|---|
| 0 | <0.04 |
| 1 | <0.04 |
| 2 | <0.04 |
| 3 | <0.04 |
| 4 | <0.04 |
| 6 | <0.04 |
| 9 | <0.04 |
| 12 | <0.04 |

Representative 4-PA values for MMB4-DMS formulations herein, where the level of solubility of the MMB4-DMS is at or below 10.0% weight, and projected out to 52 weeks, are next shown in the following Table 3. The various compositions are compared at room temperature, 40° C., and 50° C.

TABLE 3

52 Week Projected % 4-PA Values

| Sample | RT | 40 C. | 50 C. |
|---|---|---|---|
| Soybean oil-800 mg/ml-milled | 0.12 | 0.17 | 0.44 |
| PEG400-800 mg/ml-milled | 0.34 | 0.52 | 0.84 |
| PEG400-40 mg/ml-homogenized | 0.21 | — | 0.93 |
| PEG400-400 mg/ml-wet milled | 0.4 | 1.15 | 1.85 |
| Cottonseed oil-400 mg/ml-wet milled | 0.011 | 0.048 | 0.048 |
| Perfluorodecalin-400 mg/ml-wet milled | 0.018 | 0.042 | 0.046 |
| Ethanol-200 mg/ml-milled | 0.038 | 0.58 | 1.29 |

The actual stability data time points covered 4 weeks (30 days). The data was then projected using a linear excell line-fix application. Samples of particulate MMB4 DMS in the above referenced liquids also demonstrated injectability through 25-gauge needles (solid-concentration dependent) and excellent stability profile at 40 and 50° C. for a month.

What is claimed is:

1. A composition comprising:
   a bis-quaternary pyridinium-2-aldoxime salt comprising the formula:

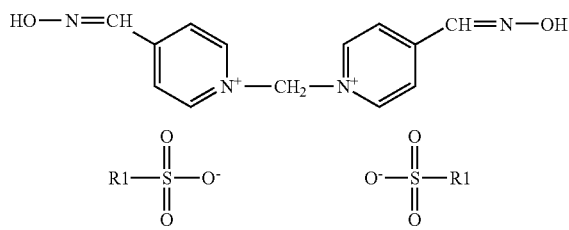

wherein R1 is independently a methyl or ethyl group wherein said salt is in particle form at a diameter of 1.0 micron to 100 microns wherein said salt indicates:
a) a plurality of distinguishing x-ray diffraction peaks at 2 Theta angles of 10-30 degrees as compared to non-distinguishing peaks at 2 Theta angles greater than 30 degrees, wherein said distinguishing x-ray diffraction peaks have relative intensity counts between 500-1500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 250 at 2 Theta angles between 30-60 degrees and wherein said salt has a particulate structure comprising cubic rectangular geometry, or
(b) a plurality of distinguishing x-ray diffraction peaks at 2 Theta angles of 10-30 degrees as compared to non-distinguishing peaks at 2 Theta angles greater than 30 degrees, wherein said distinguishing x-ray diffraction peaks have relative intensity counts between 1000-4500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 500 at 2 Theta angles between 35-60 degrees and wherein said salt has a particulate structure comprising a hexagonal structure; and
a liquid with which said salt is combined wherein the solubility of said particle in said liquid is less than or equal to 10% by weight, a two-phase (solid-liquid) system is provided, and said liquid is a fluorinated hydrocarbon.

2. The composition of claim 1 wherein said salt is present in said liquid at a level of 0.01% by weight to 80% by weight.

3. The composition of claim 1 wherein said solubility of said particle in said liquid is 0.01% by weight to 1.00% by weight.

4. The composition of claim 1 wherein said solubility of said particle in said liquid is 0.00% by weight to 0.05% by weight.

5. The bis-quaternary pyridinium-2-aldoximine salt of claim 1, wherein R1 is a methyl group.

* * * * *